United States Patent [19]

Adams et al.

[11] 4,029,793

[45] June 14, 1977

[54] SYNERGISTIC LOCAL ANESTHETIC COMPOSITIONS

[75] Inventors: Herbert J. F. Adams, Westboro; Bertil H. Takman, Worcester, both of Mass.

[73] Assignee: Astra Pharmaceutical Products, Inc., Worcester, Mass.

[22] Filed: Dec. 9, 1975

[21] Appl. No.: 639,244

Related U.S. Application Data

[60] Division of Ser. No. 369,302, June 12, 1973, Pat. No. 3,966,934, which is a continuation-in-part of Ser. No. 206,181, Dec. 8, 1971, abandoned, which is a continuation-in-part of Ser. No. 109,942, Jan. 26, 1971, abandoned.

[52] U.S. Cl. .............................. 424/251; 424/267
[51] Int. Cl.$^2$ ...................................... A61K 31/505
[58] Field of Search ........................... 424/251, 267

[56] References Cited

OTHER PUBLICATIONS

Chemical Abstracts, vol. 69 (1968) p. 9494w.
Merck Index, 8th Ed., 1968, pp. 644 and 657.

*Primary Examiner*—V. D. Turner
*Attorney, Agent, or Firm*—Brumbaugh, Graves, Donohue & Raymond

[57] ABSTRACT

A local anesthetic composition comprising a mixture in a pharmaceutically acceptable carrier of a particular toxin, namely, tetrodotoxin or desoxytetrodotoxin, and another compound, generally a con

SYNERGISTIC LOCAL ANESTHETIC COMPOSITIONS

This application is a division of application Ser. No. 369,302, filed June 12, 1973 (now U.S. Pat. No. 3,966,934), which application Ser. No. 369,302 is a continuation-in-part application of application Ser. No. 206,181, filed Dec. 8, 1971 (now abandoned), which application Ser. No. 206,181 is a continuation-in-part application of application Ser. No. 109,942 filed Jan. 26, 1971 (now abandoned).

The present invention relates to a novel anesthetic composition comprising a mixture of (1) tetrodotoxin or certain derivatives thereof and (2) another compound, generally a conventional local anesthetic compound, or a similar compound having nerve-blocking properties. The invention also relates to a process for preparing the novel anesthetic compositions and to their use for inducing anesthesia.

Toxins from marine sources of extraordinary potency have been known for many years. This application particularly concerns novel uses for tetrodotoxin.

Tetrodotoxin is obtained from the ovaries and eggs of several species of puffer fish of the suborder Gymnodontes. It is also found in certain species of California newts of the genus Taricha; and the toxin obtained from these species, known as tarichatoxin, is identical with tetrodotoxin. Tetrodotoxin has been purified, and its molecular structure is determined to be an amino perhydroquinazoline of the formula:

Tetrodotoxin and species in which it occurs are more fully described in Pharmacological Reviews, Vol. 18, No. 2, at pages 997–1049.

Experiments with isolated nerves have shown that tetrodotoxin behaves in a fundamentally different manner from local anesthetics such as procaine and cocaine. In a voltage-clamped giant axon from the squid or lobster, the latter agents reduce both inward initial sodium current and outward potassium current. With tetrodotoxin, however, inward sodium current can be reduced or even obliterated, while the outward potassium current is totally unaffected. There are few, if any, other substances in which this unique action has been established.

Tetrodotoxin has not found any practical use as an anesthetic. While the compound can be used to induce nerve blocks in laboratory animals, the anesthetic dose is slightly below the lethal dose, which precludes, as a practical matter the use of the compound as an anesthetic in its own right.

Quite surprisingly, combinations of tetrodotoxin with a local anesthetic compound have been found to possess unusual anesthetic properties. This is manifested most significantly in improved longevity of action of combinations of the toxin with local anesthetics. In these combinations, tetrodotoxin is used in concentrations below that which produces reliable nerve blocks, and well below the toxic level.

Investigation of a wide variety of local anesthetics has shown that the action of the foregoing toxin in increasing longevity of action is general. Local anesthetics may be classified by characteristic chemical type. Within each chemical type there may be unexplained variations of activity. However, in all cases investigated, each member of the groups investigated has behaved similarly when combined with the foregoing toxin. Specific classes of local anesthetics investigated include anesthetic compounds characterized by i. the aminoacylanilide group, such as lidocaine, prilocaine, bupivacaine, mepivacaine and related local anesthetic compounds having various substituents on the ring system or amine nitrogen;

The following three ester types (ii), (iii) and (iv):

(ii). the aminoalkyl benzoate group, such as procaine, chloroprocaine, propoxycaine, hexylcaine, tetracaine, cyclomethycaine, benoxinate, butacaine, proparacaine, and related local anesthetic compounds;

(iii). cocaine and related local anesthetic compounds;

(iv). the amino carbamate group such as diperodon and related local anesthetic compounds;

(v). the N-phenylamidine group, such as phenacaine and related local anesthetic compounds;

(vi). the N-aminoalkyl amide group, such as dibucaine and related local anesthetic compounds;

(vii). the aminoketone group, such as falicain, dyclonine and related local anesthetic compounds; and (viii). the aminoether group, such as pramoxine, dimethisoquine, and related local anesthetic compounds.

In each of the foregoing classes of local anesthetic compounds representative members have been enumerated. The experimental data support the conclusion that the observed effect of the toxin tested of unexpectedly extending the duration of action extend to the other known local anesthetic compounds of these groups and to the obvious modifications of the local anesthetic compounds tested. It may also be anticipated in the light of these discoveries that the novel combinations of the present invention will permit the use of concentrations of conventional local anesthetics in concentrations below the concentrations normally employed clinically. Thereby toxic manifestations sometimes observed as side effects can be minimized.

The chemical structures of some of the foregoing compounds are:

lidocaine procaine

-continued chloroprocaine, propoxycaine, hexylcaine, cocaine, tetracaine, cyclomethycaine, benoxinate, butacaine, proparacaine, diperodon, phenacaine, dibucaine, bupivacaine, mepivacaine, prilocaine, falicain -continued pramoxine $$CH_3(CH_2)_3O-\text{C}_6H_4-O(CH_2)_3N\smile O$$

Other local anesthetic compounds which may be used in combination with tetrodotoxin (TTX) are the aminoacyl anilides described in the following table.

Table A

Structure:

$$R-\underset{\underset{CH_3}{|}}{\overset{\overset{CH_3}{|}}{C_6H_3}}-NHCOCHN\underset{R^1}{\overset{R^2}{\diagdown}}R^3$$

| Compound | | R | R¹ | R² | R³ |
|---|---|---|---|---|---|
| A | 2-tert. Butylamino-2',6'-acetoxylidide | H | H | H | C(CH₃)₃ |
| B | 2-(N-n-Butyl-tert. butylamino)-2',6'-acetoxylidide | H | H | n-C₄H₉ | C(CH₃)₃ |
| C | 2-(N-n-Propyl-tert. amylamino)-2',6'-acetoxylidide | H | H | n-C₃H₇ | C(CH₃)₂C₂H₅ |
| D | 2-tert. Butylamino-2',6'-propionoxylidide | H | CH₃ | H | C(CH₃)₃ |
| E | 2-(N-Ethyl-iso-propylamino)-2',6'-propionoxylidide | H | CH₃ | C₂H₅ | CH(CH₃)₂ |
| F | 2-Methylamino-4'-(n-butoxy)-2',6'-dimethylpropion-anilide | n-C₄H₉O | CH₃ | H | CH₃ |
| G | 2-(N-Methyl-n-propylamino)-2',6'-butyroxylidide | H | C₂H₅ | CH₃ | n-C₃H₇ |
| H | 2-Dimethylamino-2',6'-acetoxylidide | H | H | CH₃ | CH₃ |
| J | 2-Ethylamino-2',6'-acetoxylidide | H | H | H | C₂H₅ |
| K | 2-Cyclobutylamino-2',6'-acetoxylidide | H | H | H | cyclobutyl |
| L | 2-tert. Amylamino-2',6'-acetoxylidide | H | H | H | C(CH₃)₂C₂H₅ |
| M | 2-(N-Methyl-n-butylamino)-2',6'-acetoxylidide | H | H | CH₃ | n-C₄H₉ |
| P | 2-(N-Ethyl-sec. butylamino)-2',6'-acetoxylidide | H | H | C₂H₅ | CH(CH₃)C₂H₅ |
| Q | 2-Amino-2',6'-propionoxylidide | H | CH₃ | H | H |
| S | 2-(N-Ethyl-n-propylamino)-2',6'-butyroxylidide | H | C₂H₅ | C₂H₅ | n-C₃H₇ |
| T | 2-Diethylamino-2',6'-valeroxylidide | H | n-C₃H₇ | C₂H₅ | C₂H₅ |

In the present invention the foregoing local anesthetics are used in a pharmaceutically acceptable carrier, such as water, water-ethanol, dextrose solutions, saline solution and blends thereof, in concentrations which are customarily used by physicians. Exemplary concentrations of local anesthetics having clinical application are:

| | % by weight |
|---|---|
| lidocaine | 0.5 – 5 |
| prilocaine | 0.5 – 5 |
| procaine | 0.5 – 5 |
| tetracaine | 0.1 – 1 |
| bupivacaine | 0.25 – 1 |
| hexylcaine | 0.5 – 2.5 |
| 2-[N-n-propyl-tert. amylamino]-2',6'-acetoxylidide | 0.1 – 2.0 |
| 2-[N-n-butyl-tert. butylamino]-2',6'-acetoxylidide | 0.1 – 2.0 |

As mentioned above, the present invention also may permit the use of the usual local anesthetics in a lower than normal concentration. For example, the combination of tetrodotoxin with lidocaine permits the latter to be used in a concentration of as little as 0.05 percent by weight.

The carrier additionally contains from 0.5 to 10, usually from 0.5 to 5, micrograms per milliliter of tetrodotoxin or from 10 to 20 micrograms per milliliter of desoxytetrodotoxin. In addition, the local anesthetic preparation may contain a vasoconstrictor, as is well known in the art, such as epinephrine, norepinephrine, phenylephrine and levonordephrine.

The local anesthetic compositions may be prepared by dissolving the local anesthetic compound, tetrodotoxin or derivative thereof and a vasoconstrictor, when present, in the carrier or in separate portions of the carrier which are thereafter blended together.

Application of the local anesthetic compositions is accomplished in the usual manner, i.e., by infiltration or injection.

EXAMPLE 1

Female Charles River rats, weighing between 100 and 200 grams, were used. These were 5 rats per group and each animal received 0.2 milliliters of drug solution in the right thigh. The injections were made in such a way as to deposit the solution around the sciatic nerve trunk close to the popliteal space. After being injected, each animal was examined at intervals to determine onset, depth, and duration of nerve block as manifested by impairment of motor function in the injected leg. Frequencies of (a) complete block, (b) partial block, and (c) slight effect on motor function were noted for each group of animals. Two end points for duration of block were used: recovery of the ability to grasp when placed on an inclined screen and complete recovery of motor function.

markedly greater than those obtained with lidocaine alone.

TABLE I

RAT SCIATIC NERVE BLOCKS

| Compound | Concentration as Base | pH | Onset (min.) | Frequency C | Frequency P | Frequency S | Duration (min.) Mean ± S.D. C.R. | Duration (min.) Mean ± S.D. R.G. |
|---|---|---|---|---|---|---|---|---|
| Tetrodotoxin | 1 µg/ml | 4.4 | — | 0/5 | 1/5 | 4/5 | — | — |
|  | 2 µg/ml | 5.4 | — | 0/5 | 2/5 | 3/5 | — | — |
|  | 5 µg/ml | 4.3 | 22 | 5/5 | — | — | — | 5.5<24 hrs |
| Lidocaine | 0.125% | 5.1 | 8 | 5/5 | — | — | 85 ± 2 | 84 ± 1.5 |
|  | 0.25% | 5.0 | 5 | 5/5 | — | — | 108 ± 22 | 99 ± 24 |
| Combinations |  |  |  |  |  |  |  |  |
| T/L | 1/0.125 | 4.9 | 5.5 | 5/5 | — | — | 309 ± 17 | 251 ± 51 |
| T/L | 2/0.125 | 4.8 | 5.0 | 4/5 | 1/5 | — | 316 ± 33 | 290 ± 46 |
| T/L | 5/0.125 | 4.6 | 3.5 | 5/5 | — | — | — | 6<24 hrs. |
| T/L | 1/0.25 | 4.7 | 4.5 | 5/5 | — | — | 5.5<24 hrs. | 299 (2) |
| T/L | 2/0.25 | 4.8 | 3.0 | 5/5 | — | — | — | 5.5<24 hrs. |
| T/L | 5/0.25 | 4.6 | 1.5 | 5/5 | — | — | — | 6< 24 hrs. |

NOTES: C = Complete block; P = Partial block; S = Slight effect; R.G. = Recovery of grasping; C.R. = Complete Recovery; T = Tetrodotoxin; L = Lidocaine. Durations are for complete blocks only. Onset times are approximate. The pH's are after addition of epinephrine; all solutions contained 1:100,000 epinephrine. Numbers of blocks are in specific instances shown in parentheses.

All solutions contained 1 to 100,000 parts epinephrine which was added immediately prior to use. All solutions were freshly prepared on the day of use.

The results are summarized in Tables I–III. Depression was occasionally noted, but there were no fatalities with these doses of tetrodotoxin.

Table I: At 1 µg/ml and 2 µg/ml tetrodotoxin produced no complete blocks. At 5 µg/ml, it produced complete blocks in all five legs injected. Mean onset time was about 20 minutes, and the blocks persisted for somewhere between 5½ hours and 24 hours. All animals were completely recovered when examined 22 to 24 hours post injection. Because this concentration of tetrodotoxin by itself produced 100 percent frequency and blocks of such long duration, there are no differences, except in onset times, between the results obtained with it alone and those obtained with the tetrodotoxin-lidocaine combination. However, the combinations of 1 µg/ml and 2 µg/ml of tetrodotoxin with lidocaine clearly show durations of block that are markedly greater than those obtained with lidocaine alone.

Table II: As in the first study, 1 µg/ml of tetrodotoxin produced no complete blocks; however, 2 µg/ml produced a complete block, with a duration of about 2 hours, in one out of five injections. The frequency of block with 3 µg/ml was only two out of five, but the block persisted for between 5 and 24 hours. In this study lower concentrations of lidocaine were used in order to ascertain whether or not the combinations show better frequencies than either tetrodotoxin or lidocaine alone.

TABLE II

RAT SCIATIC NERVE BLOCKS

| Compound | Concentration as Base | pH | Onset (min.) | Frequency C | Frequency P | Frequency S | Duration (min.) Mean ± S.D. C.R. | Duration (min.) Mean ± S.D. R.G. |
|---|---|---|---|---|---|---|---|---|
| Tetrodotoxin | 1 µg/ml | 4.6 | — | 0/5 | 0/5 | 5/5 | — | — |
|  | 2 µg/ml | 4.7 | 31 | 1/5 | 0/5 | 4/5 | 120 | 102 |
|  | 3 µg/ml | 4.5 | 56 | 2/5 | 0/5 | 3/5 | — | 5<24 hrs. |
| Lidocaine | 0.05% | 4.6 | — | 0/5 | 2/5 | 3/5 | — | — |
|  | 0.1% | 4.6 | 43 | 2/5 | 2/5 | 1/5 | 58 | 44 |
| Combinations |  |  |  |  |  |  |  |  |
| T/L | 1/0.05 | 4.6 | 31 | 1/5 | 2/5 | 2/5 | 68 | 48 |
| T/L | 2/0.05 | 4.4 | 10 | 2/5 | 2/5 | 1/5 | 255 | 176 |
| T/L | 3/0.05 | 4.5 | 16 | 3/5 | 2/5 | — | 6½<24 hrs. | 359 ± 42 |
| T/L | 1/0.1 | 4.5 | 11 | 2/5 | 3/5 | — | 144 | 93 |
| T/L | 2/0.1 | 4.6 | 6 | 4/5 | 0/5 | 1/5 | 242 ± 68 | 188 ± 83 |
| T/L | 3/0.1 | 5.2 | 14 | 4/5 | 1/5 | — | 304 (1) 6½<24 hrs. (3) | 317 ± 50 |

See Notes under Table I.

Table III: Tetrodotoxin at 3 µg/ml produced in three out of five animal blocks that lasted between 4 and 24 hours. In combinations with several local anesthetic agents, frequency was improved and onset times were shorter than with tetrodotoxin alone. All the combinations containing 1 µg/ml of tetrodotoxin exhibited durations of block much greater than obtained with the local anesthetic agents alone. The study clearly demonstrates that, in rat sciatic nerve blocks, the presence of concentrations of tetrodotoxin that by themselves are subthreshhold can cause marked increases in the durations of block of several local anesthetic agents.

TABLE III

RAT SCIATIC NERVE BLOCKS

| Compound | Concentration as Base | pH | Onset (min.) | Frequency C | P | S | Duration (min.) Mean ± S.D. C.R. | R.G. |
|---|---|---|---|---|---|---|---|---|
| Tetrodotoxin | 1 μg/ml | 4.6 | — | 0/5 | 1/5 | 4/5 | — | — |
|  | 3 μg/m. | 4.3 | 48 | 3/5 | 2/5 | — | 4<24 hrs. |  |
| Lidocaine | 2.0% | 4.4 | 2.0 | 5/5 | — | — | 172 ± 17 | 160 ± 12 |
| T/L | 1/2.0 | 4.5 | 1.5 | 5/5 | — | — | 223(2) | 188(2) |
|  |  |  |  |  |  |  | 4½<24 hrs. (3) |  |
| T/L | 3/2.0 | 4.3 | 1.5 | 5/5 | — | — | 4½<24 hrs. |  |
| Bupivacaine | 0.5% | 5.0 | 2.5 | 5/5 | — | — | 232 ± 39 | 183 ± 18 |
| T/B | 1/0.5 | 5.2 | 6.0 | 5/5 | — | — | 282 (2) | 265 ± 45 |
|  |  |  |  |  |  |  | 5<24 hrs. (3) |  |
| T/B | 3/0.5 | 5.4 | 2.5 | 5/5 | — | — | 5<24 hrs. |  |
| Prilocaine | 2.0% | 5.0 | 2.5 | 5/5 | — | — | 153 ± 16 | 123 ± 6 |
| T/Pr | 1/2.0 | 4.8 | <1.0 | 5/5 | — | — | 5<24 hrs. | 251 ± 26 |
| T/Pr | 3/2.0 | 4.8 | 2.0 | 5/5 | — | — | 5<24 hrs. |  |
| Tetracaine | 0.25% | 5.2 | 4.0 | 3/5 | 2/5 | — | 206(2) | 180(2) |
|  |  |  |  |  |  |  | 4½<24 hrs. (1) |  |
| T/Tet | 1/0.25 | 5.9 | 5.5 | 4/5 | 1/5 | — | 4<24 hrs. |  |
| T/Tet | 3/0.25 | 6.4 | 5.0 | 5/5 | — | — | 3<24 hrs. |  |

See Notes under Table I.
B = Bupivacaine; Pr = Prilocaine; Tet = Tetracaine.

EXAMPLE 2

The use of anesthetics of the present invention is also shown through peridural blocks in the cat. The surgical techniques and testing methods have been described in detail (Duce et al.: Brit. J. Anaesth., Vol. 41, 579–587 (1969) ). The animals were treated according to the following scheme in this study:

| Cat No. | Weight and Sex | Day (treatment) 1 | 2 | 3 | 4 | 5 |
|---|---|---|---|---|---|---|
| 124 | 3.6 kg F | X | L | TTX | L/TTX | X |
| 125 | 2.8 kg F | X | L | L/TTX | TTX | X |
| 127 | 4.0 kg M | X | TTX | L | L/TTX | X |
| 128 | 2.8 kg F | X | TTX | L/TTX | L | X |

X = Xylocaine HCl, 2% as salt
L = Lidocaine HCl, 2% as base
TTX = Tetrodotoxin, 1 μg/ml
F = female
M = male All animals were tested with 2 percent Xylocaine (a commercial local anesthetic composition based on lidocaine as the active ingredient) on Days 1 and 5 to ascertain the stability of the peridural cat preparation. Within the test period, laboratory-prepared samples of lidocaine were used containing only lidocaine and epinephrine or lidocaine, epinephrine and tetrodotoxin in specified proportions. Solutions were freshly prepared each day of use; epinephrine was added and the pH taken shortly before administration. The pH's of the solutions were: tetrodotoxin, 4.5–6.75; lidocaine HCl, 4.75–4.8; lidocaine/tetrodotoxin, 4.75–4.9.

The results are summarized in Table IV. In general, no overt systemic effects were noted following administration of the test solutions. Animal No. 127 exhibited salivation and emesis, with bile present, about 3 hours and 45 minutes after administration of the lidocaine/tetrodotoxin combination. However, these observations were not considered significant.

Statistical analysis of the data showed that the Xylocaine control values obtained on days 1 and 5 are not significantly different. Since tetrodotoxin alone produced no blocks, it was excluded from the analysis of variance in order to keep the variance reasonably homogeneous. A four-way analysis of variance was, therefore, done only with the data obtained with 2 percent lidocaine and with the lidocaine/tetrodotoxin combination. The durations of block with the lidocaine tetrodotoxin combination were statistically significantly longer than with lidocaine itself.

TABLE IV

PERIDURAL ANESTHESIA IN CAT

| Compound and Concentration | Deep Motor Block Duration X ± S.E. | Onset | Frequency | Block of Support of Weight Duration X ± S.E. | Onset | Frequency | Block of Flexion Reflex Duration X ± S.E. | Onset | Frequency |
|---|---|---|---|---|---|---|---|---|---|
| 2% Xylocaine (Day 1) | 119 ± 12 | 1 | 8/8 | 98 ± 13 | <1 | 8/8 | 48 ± 10 | 8 | 4/8 |
| 2% Xylocaine (Day 5) | 124 ± 11 | 1–2 | 8/8 | 106 ± 9 | 1 | 8/8 | 70 ± 17 | 7 | 6/8 |
| 1 μg/ml Tetrodotoxin | — | — | 0/8 | — | — | 0/8 | — | — | 0/8 |
| 2% Lidocaine | 115 ± 10 | 2–3 | 8/8 | 88 ± 10 | 2 | 8/8 | 66 ± 19 | 7 | 5/8 |
| Lidocaine/tetrodotoxin | 226 ± 9 | <1 | 8/8 | 188 ± 9 | <1 | 8/8 | 109 ± 8 | 7 | 7/8 |

Durations are in minutes.
Mean onset times are approximate.
Durations of block of flexion reflex in this table were calculated without zero values.
All solutions contained 1:100,000 epinephrine.

EXAMPLE 3

The effectiveness of the local anesthetics of the present invention in the absence of epinephrine is shown by the data set forth in Tables V, VI and VIII. The data summarized in these tables were obtained following the same procedures as described in Example 1.

Five separate studies were done, and a tetrodotoxin control group was run in each study. Frequency of block with tetrodotoxin ranged from 0/5 to 3/5, and durations ranged from about 180 to 240 minutes. Frequency of block was 5/5 with all combinations except that containing phenacaine (Table VI). The one partial block in this case may have been due to failure to inject the solution sufficiently close to the sciatic nerve trunk. The frequency of block with the diperodon-tetrodotoxin, cyclomethycaine-tetrodotoxin and dibucaine-tetrodotoxin were better than with diperodon, cyclomethycaine, dibucaine or tetrodotoxin by itself.

In all cases, the combinations produced durations markedly longer than obtained with the local anesthetics alone. The durations of tetrodotoxin alone were closer to those with the combinations; the frequencies were consistently lower than those produced by the combinations.

EXAMPLE 4

The use of desoxytetrodotoxin was tested following the procedure described in Example 1. The desoxy derivative was substituted for the tetrodotoxin referred to in Example 1. Desoxytetrodotoxin was tested, without epinephrine, in rat sciatic nerve blocks. At concentrations of 5, 10 and 20 $\mu$g/ml it produced no blocks. The duration of block of a combination containing 2 percent lidocaine and 5 $\mu$g/ml of desoxytetrodotoxin was not significantly different from that of 2 percent lidocaine alone. However, combinations containing 10 and 20 $\mu$g/ml of desoxytetrodotoxin produced blocks that were significantly longer (1.4–1.6 times) than that of lidocaine alone ($0.008 > p > 0.016$).

TABLE V

RAT SCIATIC NERVE BLOCKS

| Compound | % Conc. as base | pH | Onset (min.) | Frequency C | Frequency P | Duration (min.) Mean ± S.D. C.R. | Duration (min.) Mean ± S.D. R.G. |
|---|---|---|---|---|---|---|---|
| Lidocaine | 2.0 | 4.8 | 1 | 5/5 | — | 108 ± 48 | 103 ± 37 |
| Lidocaine/TTX | 2.0 | 4.8 | <1 | 5/5 | — | 385 ± 25 | 348 ± 17 |
| Procaine | 2.0 | 5.5 | 2.5 | 5/5 | — | 62 ± 7 | 60 ± 7 |
| Procaine/TTX | 2.0 | 5.5 | 2 | 5/5 | — | 356 ± 53 | 314 ± 58 |
| Chloroprocaine | 2.0 | 5.4 | 1.5 | 5/5 | — | 111 ± 65 | 87 ± 36 |
| Chloroprocaine/TTX | 2.0 | 5.3 | 1 | 5/5 | — | 351 ± 73 | 325 ± 46 |
| Tetrodotoxin | 2 $\mu$g/ml | 6.0 | 13 | 2/5 | 0/5 | 242 ± 4 | 226 ± 5 |
| Diperodon | 0.25 | 5.4 | 22 | 2/5 | 0/5 | 124 | 64 |
| Diperodon/TTX | 0.25 | 5.4 | 9 | 5/5 | — | 332 ± 59 | 286 ± 33 |
| Propoxycaine | 0.25 | 5.4 | 4 | 5/5 | — | 64 ± 12 | 52 ± 15 |
| Propoxycaine/TTX | 0.25 | 5.5 | 1.5 | 5/5 | — | 262 ± 91 | 239 ± 102 |
| Hexylcaine | 0.5 | 5.6 | 3 | 5/5 | — | 112 ± 12 | 99 ± 17 |
| Hexylcaine/TTX | 0.5 | 5.5 | 4.5 | 5/5 | — | 339 ± 17 | 303 ± 12 |
| Cocaine | 0.25 | 6.1 | 4.5 | 5/5 | — | 98 ± 9 | 86 ± 17 |
| Cocaine/TTX | 0.25 | 5.6 | 5 | 5/5 | — | (1 day) | 361 ± 28 |
| Tetrodotoxin | 2 $\mu$g/ml | 6.1 | 16 | 2/5 | 1/5 | 216 ± 51 | 161 |

TTX = Tetrodotoxin, 2 $\mu$g/ml; C = Complete block; P = Partial block; C.R. = Complete recovery of normal motor function; R.G. = Recovery of grasping; Durations are for complete blocks only; Onset times are approximate.

TABLE VI

RAT SCIATIC NERVE BLOCKS

| Compound | % Conc. as base | pH | Onset (min.) | Frequency C. | Frequency P | Duration (min.) Mean ± S.D. C.R. | Duration (min.) Mean ± S.D. R.G. |
|---|---|---|---|---|---|---|---|
| Phenacaine | 0.25 | 5.6 | 4.5 | 5/5 | — | 78 ± 32 | 70 ± 32 |
| Phenacaine/TTX | 0.25 | 5.5 | 8 | 4/5 | 1/5 | 282 ± 74 | 253 ± 71 |
| Benoxinate | 0.25 | 5.6 | 3 | 5/5 | — | 116 ± 24 | 97 ± 20 |
| Benoxinate/TTX | 0.25 | 5.6 | 8 | 5/5 | — | 320 ± 54 | 285 ± 58 |
| Butacaine | 0.25 | 5.8 | 6 | 4/5 | 1/5 | 73 ± 7 | 67 ± 2 |
| Butacaine/TTX | 0.25 | 5.6 | 5 | 5/5 | — | 241 ± 24 | 204 ± 37 |
| Tetrodotoxin | 2 $\mu$g/ml | 6.1 | 18 | 1/5 | — | 181 | 150 |
| Proparacaine | 0.5 | 6.0 | 1.5 | 5/5 | — | 98 ± 20 | 89 ± 14* |
| Proparacaine/TTX | 0.5 | 6.1 | 2 | 5/5 | — | 429 ± 41 | 415 ± 50* |
| Tetrodotoxin | 2 $\mu$g/ml | 6.2 | 13 | 3/5 | 2/5 | 222 ± 48 | 206 ± 42 |

TTX = Tetrodotoxin, 2 $\mu$g/ml; C = Complete block; P = Partial block; C.R. = Complete recovery of normal motor function; R.G. = Recovery of grasping; Durations are for complete blocks only; Onset times are approximate.
*Means of 3 animals; 2/5 died.

TABLE VII

RAT SCIATIC NERVE BLOCKS

| Compound | % Conc. as base | pH | Onset (min.) | Frequency C | Frequency P | Duration (min.) Mean ± S.D. C.R. | Duration (min.) Mean ± S.D. R.G. |
|---|---|---|---|---|---|---|---|
| Cyclomethycaine | 0.125 | 5.1 | 17 | 1/5 | 4/5 | 145 | 115 |
| Cyclomethycaine/TTX | 0.125 | 5.2 | 5 | 5/5 | — | 273 ± 43 | 231 ± 41 |
| Dibucaine | 0.125 | 5.4 | 6 | 3/5 | 1/5 | 125 ± 22 | 108 ± 25 |
| Dibucaine/TTX | 0.125 | 5.4 | 6 | 5/5 | — | 324 ± 47 | 272 ± 56 |
| Tetrodotoxin | 2 $\mu$g/ml | 5.6 | — | 0.5 | 1/5 | — | — |

TTX = Tetrodotoxin, 2 $\mu$g/ml; C = Complete block; P = Partial block; C.R. = Complete recovery of normal motor function; R.G. = Recovery of grasping; Durations are for complete blocks only; Onset times are approximate.

This result is to be expected based on the tests of tetradotoxin in view of the lower activity shown by the desoxy derivative in toxicity tests. Literature on the toxicity of tetrodotoxin and its desoxy derivative reports the latter to be between one quarter and one tenth as toxic as its present toxin.

EXAMPLE 5

Method: Mature male beagles are surgically prepared by implantation of a cannula into a lumbar vertebra so that drug solutions may be administered into the peridural space. After administration of local anesthetic solutions, the animals are examined at intervals for duration of loss of pain in the scrotal area and in the digits of the hind limbs as well as for loss of ability to suport their weight.

Response to the awareness of pain stimuli in scrotal area is a test for anesthetic block in spinal roots L3-4 and S1-2-3. These roots are the furthest removed from the point of injection (L6) and, therefore, least likely to be affected by the anesthetic. Return of response to pain in the scrotum is often the first sign of recovery and indicates recession of anesthesia to at least L4 anteriorly and S2 posteriorly.

TABLE VIII

PERIDURAL ANESTHESIA IN DOGS

| | Onset: mean and range | | | Duration: mean and range | | |
|---|---|---|---|---|---|---|
| Compound and Concentration | Digital Pain | Scrotal Pain | Weight Support | Digital Pain | Scrotal Pain | Weight Support |
| Lidocaine 2% | 7 | 8 | <5 | 127 | 111 | 137 |
| (n = 3) | | | | 76–162 | 62–152 | 108–162 |
| Tetrodotoxin | 19.5 | 15* | <17 | 225 | | 406 |
| 4 μg/ml | | | | | | |
| (n = 2) | 19–20 | | | 87–350 | 0–125 | 339–473 |
| Lidocaine 2% | | | | 316 | 301 | 462 |
| Tetrodotoxin | <5 | <5 | <3 | 245–387 | 235–367 | 400–525 |

*One animal only; no anesthesia in second animal.
Onsets and durations are in minutes. All Solutions contained 1:100,000 epinephrine. Volume of administration = 5 ml. n = number of animals
NOTE:
(1) With lidocaine onset is rapid, frequency of block is 100%, but durations are short.
(2) With tetrodotoxin durations are long, but onset is slow and frequency of block of scrotal pain is poor.
(3) With the combination onset is rapid, frequency is 100% and durations are long.

EXAMPLE 6

Following the method described in Example 1 above, various local anesthetic compounds alone, TTX alone and combinations of the compounds with TTX were tested for their ability to block the rat sciatic nerve. TTX was used uniformly in the amount of 2 μg/ml. Each of the compositions tested contained epinephrine in concentration of 1:100,000. The results are presented in Table IX. In the case of compound A in 0.5% concentration, duration was about 126 minutes. TTX alone was about 295 minutes but frequency was not good. In combination, frequency was good and duration was greater than 420 minutes.

In the case of compound D at 0.25% concentration, duration was about 128 minutes alone but greater than 420 minutes in combination with TTX. In the case of compound E at 0.25% concentration, no blocks were observed alone, but in combination with TTX the duration was about 148 minutes. In the case of compound F alone at 0.125% concentration, duration was only 78 minutes with poor frequency, whereas in combination with TTX duration was greater than 322 minutes and frequency had improved. For compound G at 0.5% concentration, duration was 104 minutes alone and about 286 minutes in combination with TTX.

It should be noted moreover that in the case of TTX alone, the frequency and duration were quite variable ranging from zero frequency to 4 out of 5, and ranging from zero duration to 295 minutes or more.

Table IX

Rat Sciatic Nerve Blocks

Tetrodotoxin (TTX) (2 μg/ml) and Various Local Anaesthetic Compounds. Epinephrine concentration 1:100,000.

| Compound | Frequency | Duration (min.) Mean ± S.D. |
|---|---|---|
| TTX | 2/5 | 295* |
| A (0.5%) | 5/5 | 126 ± 12 |
| TTX + A (0.5%) | 5/5 | >420, <24 hrs.** |
| A (1.0%) | 5/5 | 157 ± 18 |
| TTX + A (1.0%) | 5/5 | >420, <24 hrs. |
| TTX | 4/5 | 316 ± 10* |
| D (0.25%) | 5/5 | 128 ± 13 |
| TTX + D (0.25%) | 5/5 | >420, <24 hrs. |
| D (0.5%) | 5/5 | 133 ± 7 |
| TTX + D (0.5%) | 5/5 | >420, <24 hrs. |
| TTX | 0/6 | 0 |
| E (0.25%) | 0/6 | 0 |
| TTX + E (0.25%) | 4/6 | 148 ± 27 |
| TTX | 0/5 | 0 |
| F (0.125%) | 1/5 | 78 |
| TTX + F (0.125%) | 3/5 | >322 min. |
| TTX | 0/5 | 0 |
| G (0.5%) | 5/5 | 104 ± 14 |
| TTX + G (0.5%) | 4/5 | 286 ± 197 |

*One animal blocked >420 min.
**>420, <24 hrs. means that the animals returned to normal during a period when they were not observed, this period being longer than 7 hrs. and shorter than 24 hrs.

EXAMPLE 7

In vitro tests were made on the isolated intact frog sciatic nerve using compounds B, C and lidocaine alone and in combination with TTX. The results and the method followed are presented in Table X. The reduction in the action potential of compound B alone was 22% and for TTX alone it was 15%, as compared with a reduction of 94% for the combination. For compound C alone the reduction was 24%, and for TTX alone 29%, whereas the combination again reduced the potential by 94%. For lidocaine and TTX each alone the reductions were 15% and 7%, respectively, as compared with a reduction of 61% for the combination of the two.

Table X

Block of Isolated Intact Frog Sciatic Nerve.

| Compound | pH | Concn. mM | Percent reduction of the action potential. Mean and range | Number of experiments |
|---|---|---|---|---|
| B | 5.6 | 0.625 | 22 (10–38) | 16 |
| TTX | 5.6 | $3 \cdot 10^{-4}$ | 15 (8– ) | 17 |
| B + TTX | 5.6 | as above | 94 (80–100) | 17 |
| C | 5.6 | 0.156 | 24 (15–52) | 8 |
| TTX | 5.6 | $3 \cdot 10^{-4}$ | 29 (14–80*) | 6 |
| C + TTX | 5.6 | as above | 94 (78–100) | 12 |
| Lidocaine | 7.0 | 0.625 | 15 (6–30) | 6 |
| TTX | 7.0 | $1 \cdot 10^{-4}$ | 7 (2–12) | 6 |
| Lidocaine + TTX | 7.0 | as above | 61 (20–100) | 12 |

*Occasionally a high value is observed, probably caused by a minute damage to the nerve sheath during dissection. It takes about 50 times the concentration of TTX which is necessary to block a desheathed nerve in order to obtain the same degree of block of an intact (sheathed) nerve.

Method: The method is essentially as described by A. P. Truant, Arch. Int. Pharmacodyn. 115, 483–497 (1958).

Sciatic nerve trunks of *Rana pipiens* are prepared by dissecting the nerve from its roots in the spinal cord to the ankle and placing it on silver-silver chloride electrodes so that stimulation and recording of the action potential can be performed during the course of application of the test compounds and during the recovery period. The bathing solution is Tasaki Ringer's. The observations lasted for 40 minutes allowing the action potentials to reach essentially a stable value (equilibrium).

EXAMPLE 8

Using the procedure described in Example 1 above, the effect of several known vasoconstrictors on rat sciatic nerve blocks was investigated using lidocaine (0.125%) and tetrodotoxin (2 μg/ml) in combination. The results are given in Table XI. Without any vasoconstrictors, the frequency was very poor and the duration of block was 174 minutes. With phenylephrine, levonordefrin, or epinephrine, however, frequency was greatly improved and duration had about doubled.

Table XI

Effect of Vasoconstrictors on Rat Sciatic Nerve Blocks Obtained with Lidocaine (0.125%) and Tetrodotoxin (2 μg/ml).

| Vasoconstrictor | Concn. | Frequency | Duration of Block (min.) Mean ± S.D. |
|---|---|---|---|
| None | — | 1/5 | 174 |
| Phenylephrine | 1:20,000 | 5/5 | 377 ± 27 |
| Levonordefrin | 1:20,000 | 5/5 | 354 ± 12 |
| Epinephrine | 1:200,000 | 5/5 | 368 ± 24 |

EXAMPLE 8a

Using the procedure described in Example 1, except that no epinephrine was added to the solutions tested, the local anesthetics falicain and pramoxine were tested for blockage on the rat sciatic nerve alone and in combination with TTX at 2 μg/ml. The results are presented in the following Table XII.

TABLE XII

Rat Sciatic Nerve Blocks

| | Frequency | Duration |
|---|---|---|
| 0.25% falicain | 5/5 | 55 ± 22 |
| 0.25% falicain ± TTX, 2 μg/ml | 5/5 | 116 ± 71 |
| 0.25% pramoxine | 0/5 | 0 |
| 0.25% pramoxine ± TTX, 2 μg/ml | 2/5 | 190 ± 76 |
| TTX, 2 μg/ml | 0.5 | 0 |

It will be observed that the ingredients were tested at dose level that did not result in any anesthesia at all for two of them, and only 55 min. for the third one, whereas the combination gave anesthesia about 2 to 3 hrs. The frequency of complete block was raised from 0 to 40% in the case of pramoxine.

Compounds A, B, C, D and L described in Table A above are made by the procedure described in U.S. patent application Ser. No. 369,146, filed June 12, 1973, which is a continuation-in-part of Ser. No. 325,378, filed Jan. 22, 1973, now abandoned, both assigned to the same assignee as the present application, which disclosure is incorporated herein by reference.

The method of preparing compounds S and T is disclosed in U.S. patent application Ser. No. 164,022 filed July 19, 1971, now U.S. Pat. No. 3,812,147, which is incorporated herein by reference.

The method of preparing compound Q is disclosed in U.S. patent application Ser. No. 321,590 filed Jan. 8, 1973, now abandoned, which is incorporated herein by reference.

Compounds H, J and M and mepivacaine are known compounds disclosed in the published literature.

EXAMPLE 9

Synthesis of 2-(N-ethyl-isopropylamino)-2',6'-propionoxylidide (Compound E)

A mixture of 12.81 g (0.050 mole) of 2-bromo-2',6'-propionoxylidide, 11.31 g (0.130 mole) ethyl-isopropylamine and 30 ml dry toluene was heated in a glass-lined, stainless-steel pressure vessel at 105° for 20 hours. After cooling to 25°, the brown rection mixture was filtered, extracted three times with a total of 50 ml of 3 N HCl. The aqueous solution was heated to 75° for 10 minutes with decolorizing carbon and then filtered. To the chilled solution was added 10 ml concentrated $NH_3$. The product which precipitated was filtered, washed, and dried. Yield: 6.93 g (52.9%) m.p. 50–2°.

Anhydrous ethereal HCl was added to 6.90 g of the above base dissolved in 100 ml dry ether until the solution was acidic to moist pH paper, giving 6.15 g of tacky brown material, m.p. 191°–201°. The hydrochloride was recrystallized from a mixture of butanone and alcohol. Yield: 6.02 g, m.p. 207.5°–209°.

Analysis: Calc'd for $C_{16}H_{27}ClN_2O$: C 64.30, H 9.11, N 9.37, Cl 11.86. Found: C 64.16; H 9.16, N 9.49, Cl 12.09.

EXAMPLE 10

A. Synthesis of 2-Bromo-4'-butoxy-2',6'-dimethyl propionanilide

To a chilled (ca 10°) solution of 50.7 g (0.263 mole) of 4-butoxy-2,6-dimethylaniline [Büchi et al., Helv. Chim. Acta, 34, 278 (1951)] in 224 ml glacial acetic acid was added rapidly 62.4 g (.289 mole) of 2-bromopropionyl bromide and immediately thereafter a chilled (ca 5°) solution of 87.2 g sodium acetate trihydrate in 362 ml water. This mixture was shaken for ½ hour, filtered, washed with water until the washers were neutral, and dried in vacuo over silica gel and KOH; yield 68.9 g (71.6%); m.p. 132.5°–133.5°. The product was recrystallized from 95% ethanol; m.p. 135.5°–136°.

Analysis: Calc'd for $C_{15}H_{22}NO_2Br$: C 54.87, H 6.76, Br 24.34. Found: C 55.06, H 6.22, Br 24.69.

B. Synthesis of 2-Methylamino-4'-butoxy-2',6'-dimethyl-propionanilide (Compound F)

To a cold stirred solution of 14.8 g. of monomethyl amine in 250 ml dry benzene was added (portionwise, keeping temperature below 10°) 19.5 g (0.0594 mole) of 2-bromo-4'-butoxy-2', 6'-dimethyl propionanilide (made according to the procedure in the first part of this example); this dissolved readily forming a clear solution. The mixture was heated to 70° for ca 1 hr. with stirring, at which point a white precipitate had separated and reflux became so vigorous that the reaction had to be controlled by external cooling.

The precipitated methylammonium bromide was filtered off. Excess amine and solvent were removed in vacuo from the filtrate, giving a white residue which was dissolved in 120 ml 0.5 M HCl and filtered. The filtrate was extracted with 3 × 25 ml. ether; and the ether extracts discarded.

The aqueous phase was alkalized to pH 11, and extracted with ether; the combined extracts were dried ($Na_2SO_4$), filtered, and evaporated, giving a yield of 8.7 g (52.7%); m.p. 107°–107.5°. Recrystallization from cyclohexane did not effect the melting point.

Analysis: calc'd. for $C_{16}H_{26}N_2O_2$ : C 69.0; H 9.41 ; N 10.06. Found: C 69.0; H 9.17; N 10.06.

EXAMPLE 11

Synthesis of 2-(N-Methyl-n-propylamino)-2',6'-butyroxylidide (Compound G)

To a stirred solution of N-methyl-n-propylamine (9.10 g, 0.125 mole) in 175 ml of anhydrous benzene was added 2-iodo-butyro-2',6'-xylidide (13.2 g, 0.0415 mole). The mixture was allowed to reflux for 5 hrs.

The reaction mixture was extracted with 1 M HCl. After filtration to remove trace insolubles, the pH was adjusted to 9 with 7 M NaOH, which caused the formation of a light-yellow waxy solid. The latter was filtered, washed with water, and dried; yield 4.00 g (36.7%).

This base was converted to the hydrochloride salt with ethereal HCl. The hydrochloride was twice-recrystallized from ethanol/ether, affording cyrstals melting at 214°–215° C.

Analysis: Calc'd. for $C_{16}H_{27}ClN_2O$: C 64.3; H 9.11; Cl 11.86 Found: C 64.4; H 9.01; Cl 11.80.

EXAMPLE 12

Synthesis of 2-Cyclobutylamino-2',6'-acetoxylidide (Compound K).

To a solution of cyclobutylamino (39.8 g) in 600 ml benzene was added 2-chloro-2'-acetoxylidide (49.4 g), slowly, with stirring, and the mixture was refluxed for about 5 hrs. After cooling, the mixture was filtered to remove the cyclobutylammonium chloride formed.

The filtrate was stripped of solvent and excess amine in vacuo; leaving a crude residue.

The residue was dissolved in 0.5 M hydrochloric acid, the solution was made alkaline with sodium hydroxide solution and the base was extracted carefully with ether. The ether solution was dried ($Na_2SO_4$), the ether and low-boiling components were evaporated in vacuo at 40°–50° C and the residue converted to a hydrochloride by addition of ethereal hydrogen chloride to its filtered ether solution. From the hydrochloride the base was obtained by dissolution in water, addition of sodium hydroxide solution to alkaline pH, extraction with ether, drying of the ether extract ($Na_2SO_4$), filtering, and evaporation of the ether. The base could be recrystallized from cyclohexane, petroleum ether (b.p. 60°–110° C), or heptane. The melting point was found to be 75°–78° C.

Analysis: Calc'd. for $C_{14}H_{20}N_2O$ : C 72.4, H 8.68, N 12.06. Found: C 72.4, H 8.88, N 11.93.

EXAMPLE 13

A. Synthesis of 2-(sec-butylamino)-2',6'-acetoxylidide

To a solution of 62.2 g of sec-butylamine in 500 ml benzene was added slowly 41.5 g of 2-chloro-2',6'-acetoxylidide. The mixture was heated to reflux for 7 hours and allowed to cool overnight. The precipitate of sec-butyl amine hydrochloride that formed was filtered off and the filtrate was evaporated to an oily residue. The residue was dissolved in ether, and the solution was filtered, dried ($Na_2SO_4$), and evaporated to an oily residue (45.7 g). This crude product was distilled under vacuum, giving an oily liquid that solidified when chilled. Yield: 38.5 g (78%); b.p. 146°/0.05 mm; m.p. 44.5°–45.5°.

Analysis: Calc'd. for $C_{14}H_{22}N_2O$ : C 71.75, H 9.46, H 11.96. Found: C 71.99, H 9.35, N 12.12. The hydrochloride melted at 176.5°–178.5°.

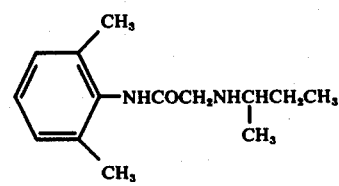

B. Synthesis of 2-(N-ethyl-sec-butylamino)-2',6'-acetoxylidide (Compound P)

To 140 g of diethyl sulfate was added 30.5 g of 2-(sec-butylamino)-2',6'-acetoxylidide (made by the method described in the first part of this example). The mixture was heated to 100°–110° for 5 hours and cooled. Water and 5 N HCl were added to pH 2, forming a second phase. After stirring, the aqueous phase (pH 2) was separated, washed with two 100 ml portions of ether and brought up to pH 9 with concentrated $NH_3$. The basic aqueous phase was extracted with five 100 ml portions of ether. The solvent was stripped in vacuo from the combined ether phases, leaving a solidifying oil which was dissolved in ether, dried ($Na_2SO_4$), filtered, and evaporated in vacuo. Yield: 26.2 g (76.8%); m.p. 50.5°–54.5° . The product was twice distilled under high vacuum : b.p. 147°/0.025 mm; 165°/0.4 mm. Yield of redistilled product: 21.4 g (62.7%).

Analysis: Calc'd. for $C_{16}H_{26}N_2O$ : C 73.23%, H 9.99%, N 10.68%. Found: C 73.06%, H 9.66%, N 10.47%.

We claim:

1. An injectable local anesthetic composition having long-lasting local anesthetic effect which is a solution consisting essentially of a pharmaceutically acceptable carrier having dissolved therein
   a. a heterocyclic aminoacyl anilide local anesthetic compound in a concentration of from 0.05 to 5% by weight of the carrier and
   b. a toxin selected from the group consisting of from 0.5 to 10 micrograms of tetrodotoxin per milliliter of the carrier and from 10 to 20 micrograms of desoxytetrodotoxin per milliliter of the carrier.

2. The composition as defined by claim 1 wherein said component (b) is tetrodotoxin.

3. The composition as defined by claim 1 wherein said component (b) is desoxytetrodotoxin.

4. The composition as defined by claim 2 wherein the heterocyclic aminoacyl anilide is bupivacaine.

5. The composition as defined by claim 2 wherein the heterocyclic aminoacyl anilide is mepivacaine.

6. The composition as defined by claim 1 which further contains an effective amount of a vasoconstrictor.

7. A method of inducing anesthesia in mammals comprising administering to the mammal to be anesthetized an effective amount of an injectable local anesthetic composition having long-lasting local anesthetic effect which is solution consisting essentially of a pharmaceutically acceptable carrier having dissolved therein
   a. a heterocyclic aminoacyl anilide local anesthetic compound in a concentration of from 0.05 to 5% by weight of the carrier and
   b. a toxin selected from the group consisting of from 0.5 to 10 micrograms of tetrodotoxin per milliliter of the carrier and from 10 to 20 micrograms of desoxytetrodotoxin per milliliter of the carrier.

8. The method as defined by claim 7 wherein said component (b) is tetrodotoxin.

9. The method as defined by claim 7 wherein said component (b) is desoxytetrodotoxin.

10. The method as defined by claim 8 wherein the heterocyclic aminoacyl anilide is bupivacaine.

11. The method as defined by claim 8 wherein the heterocyclic aminoacyl anilide is mepivacaine.

12. The method as defined by claim 7 wherein said composition further contains an effective amount of a vasoconstrictor.

* * * * *

UNITED STATES PATENT AND TRADEMARK OFFICE
CERTIFICATE OF CORRECTION

PATENT NO. : 4,029,793
DATED : June 14, 1977
INVENTOR(S) : Herbert J. F. Adams et al It is certified that error appears in the above-identified patent and that said Letters Patent are hereby corrected as shown below:

Col. 5, the following formula in Table A

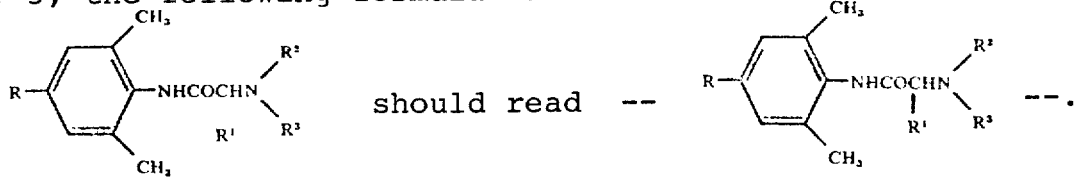

Col. 10, line 62, "VIII" should be -- VII --. Col. 13, line 2, "tetradotoxin" should be -- tetrodotoxin --; line 6, "present" should be -- parent --; line 17, "the" should be -- and --; in Table VIII, after line 7 under the caption "Compound and Concentration", there should be inserted -- 4 µg/ml. --. (n=2)

Col. 16, line 45, "rection" should be -- reaction --. Col. 17, line 5, "washers" should be -- washes --. Col. 18, lines 36 and 37, "H 11.96" should be -- N 11.96 --. Col. 20, line 5, before "solution" insert -- a --.

Signed and Sealed this

Thirteenth Day of December 1977

[SEAL]

Attest:

RUTH C. MASON
Attesting Officer

LUTRELLE F. PARKER
Acting Commissioner of Patents and Trademarks